United States Patent [19]

Noglami et al.

[11] Patent Number: 4,939,467
[45] Date of Patent: Jul. 3, 1990

[54] FUEL SENSOR FOR SENSING THE MIXTURE RATIO OF GASOLINE AND METHANOL

[75] Inventors: Yasuhiro Nogami; Hisao Nunokawa, both of Tokyo, Japan

[73] Assignee: Calsonic Corporation, Tokyo, Japan

[21] Appl. No.: 379,883

[22] Filed: Jul. 14, 1989

[30] Foreign Application Priority Data

Jul. 21, 1988 [JP] Japan .................. 63-183765

[51] Int. Cl.⁵ .................. G01R 27/26; G01N 27/22
[52] U.S. Cl. ................... 324/663; 324/690; 324/449; 324/450; 73/61.1 R
[58] Field of Search ........... 324/61 R, 61 P, 60 CD, 324/61 QS, 663, 678, 690; 73/61.1 R

[56] References Cited

U.S. PATENT DOCUMENTS

| | | | |
|---|---|---|---|
| 3,215,900 | 11/1965 | Harvey | 324/61 P |
| 3,368,147 | 2/1968 | Graham | 324/61 P |
| 3,778,706 | 12/1973 | Thompson | 324/61 R |
| 4,075,680 | 2/1978 | Shipp, Jr. | 324/61 P X |
| 4,540,936 | 9/1985 | Walsh | 324/61 P |
| 4,711,244 | 12/1987 | Kuzara | 324/61 QS |

FOREIGN PATENT DOCUMENTS 56-138431 10/1981 Japan .

Primary Examiner—Reinhard J. Eisenzopf
Assistant Examiner—Jack B. Harvey
Attorney, Agent, or Firm—Foley & Lardner, Schwartz, Jeffery, Schwaab, Mack, Blumenthal & Evans

[57] ABSTRACT

A fuel sensor for sensing a mixing ratio of a given liquid in a mixed fuel comprises a housing; a structure housed in the housing, the structure having a fuel passage formed therethrough; and an electrode assembly housed in the housing and held by the structure, the electrode assembly including at least one pair of probe portions which are exposed to the fuel passage. The full sensor also includes an output control circuit housed in the housing, the output control circuit issuing an amplified voltage output which varies in accordance with a small information signal applied to an input portion of the output control circuit; and an electrically conducting member housed in the housing and electrically connecting the electrode assembly to the input portion of the output control circuit, so that the output control circuit issues an amplified voltage output which varies in accordance with a capacitance established between the paired probe portions.

8 Claims, 4 Drawing Sheets

FUEL SENSOR FOR SENSING THE MIXTURE RATIO OF GASOLINE AND METHANOL

BACKGROUND OF THE INVENTION

1. Field of the Invention

The present invention relates in general to fuel sensors, and more particularly to fuel sensors of a type which senses the mixing ratio of methanol in a mixture of gasoline and methanol.

2. Description of the Prior Art

For dealing with the energy crisis and air polution problem, it has been proposed to use as the fuel of an automotive internal combustion engine a mixed fuel, such as a mixture of gasoline and methanol. Japanese Patent First Provisional Publication 56-138431 shows one of the engine systems of such type, in which a fuel injection system is used. In the engine system of this publication, a measure is employed in which for practically operating the engine on the methanol-mixed gasoline, the fuel injection amount and ignition timing are controlled in accordance with the mixing ratio of methanol in the mixed fuel, which ratio is measured by a fuel sensor disposed in a fuel container.

The fuel sensor is of a capacitance type which comprises a pair of spaced electrode plates submerged in the fuel. The dielectric constant of the fuel is detected by measuring the capacitance established between the electrode plates, and the mixing ratio of methanol is derived from the dielectric constant.

In operation, the signal representative of the capacitance established between the electrode plates is transmitted through elongate lead wires to a separate control circuit where subsequent signal conversion and processing are carried out.

However, usage of such lead wires tends to induce noise on the signal. That is, since the capacitance practically established between the electrode plates is quite small (that is, of the order of $10^{-12}$ F), the signal representative of the capacitance is greatly affected by noises and floating capacitance thereby causing a considerable error in measuring the mixing ratio of methanol in the fuel.

SUMMARY OF THE INVENTION

It is therefore an object of the present invention to provide a fuel sensor which is free of the above-mentioned drawback.

According to the present invention, there is provided a fuel sensor in which both an electrode assembly and an output control means are installed in a common housing thereby to shorten the length of conductors by which the electrode assembly and the control means are electrically connected.

According to the present invention, there is provided a fuel sensor in which fastening screws for fixing the electrode assembly in the common housing are used for electrically connecting the electrode assembly to the control means.

According to the present invention, there is provided a fuel sensor for sensing a mixing ratio of a given liquid in a mixed fuel. The fuel sensor comprises a housing; a structure housed in the housing, the structure having a fuel passage formed therethrough; an electrode assembly housed in the housing and held by the structure, the electrode assembly including at least one pair of probe portions which are exposed to the fuel passage; an output control means housed in the housing, the output control means issuing an amplified voltage output which varies in accordance with a small information signal applied to an input portion of the output control means; and electrically conducting means housed in the housing and electrically connecting the electrode assembly to the input portion of the output control means, so that the output control means issues an amplified voltage output which varies in accordance with a capacitance established between the paired probe portions.

BRIEF DESCRIPTION OF THE DRAWINGS

Other objects and advantages of the present invention will become apparent from the following description when taken in conjunction with the accompanying drawings, in which.

DETAILED DESCRIPTION OF THE INVENTION

Figure 1:
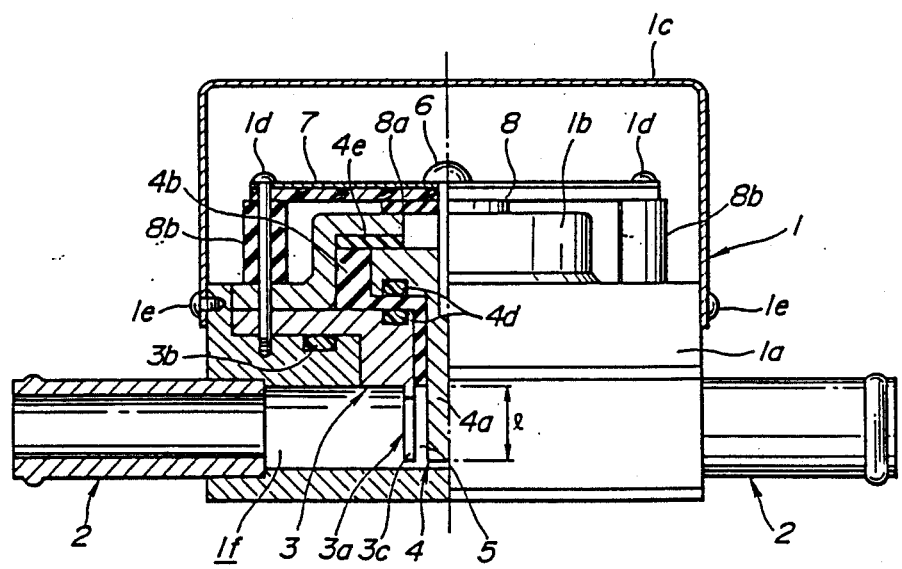
FIG. 1 is a partially sectioned front view of a fuel sensor, ,which is a first embodiment of the present invention.

Referring to FIGS. 1 to 5, particularly FIG. 1, there is shown a fuel sensor which is a first embodiment of the present invention, which is applicable to an automotive engine system having a known fuel injection system mounted therein.

Designated by numeral 1 is a housing of the sensor, which comprises a lower case 1a, an upper case 1b and a cover 1c. The upper case 1b is mounted on the lower case 1a and secured to the same by means of fastening screws 1d, and the cover 1c is secured to the lower case 1a, by means of fastening screws 1e, in a manner to house therein the upper case 1b.

The lower case 1a has a fuel passage 1f formed therethrough. The fuel passage 1f has inlet and outlet portions to which respective pipes 2 are connected. One of the pipes 2 is connected with a fuel tube (not shown) which leads to a fuel tank (not shown) and the other pipe is connected with the other fuel tube which leads to the fuel injection valves of the engine system.

Within the housing 1, there are arranged a pair of electrodes 3 and 4, one 3 being a side electrode and the other 4 being a center electrode. These electrodes 3 and 4 have respective probe portions 3a and 4a exposed to the fuel passage 1f of the lower case 1a. That is, the side electrode 3 is connected through a seal ring 3b to the lower case 1a and has a cylindrical hollow probe portion 3a exposed to the fuel passage 1f. The center electrode 4 is connected through an electrically insulating member 4e to the upper case 1b and has a cylindrical solid probe portion 4a concentrically disposed in the cylindrical hollow probe portion 3a of the side electrode 3. Thus, there is formed between the cylindrical hollow probe portion 3a and the cylindrical solid probe portion 4a a cylindrical space 5. An electrically insulating member 4b is disposed between the side and center electrodes 3 and 4 to assure electric insulation therebetween. Designated by numerals 4d are seal rings which are arranged having the insulating member 4b compressed therebetween As shown in FIG. 1, the fixing of the side electrode 3 to the lower case 1a is achieved by the afore-mentioned fastening screws 1d, while the fixing of the center electrode 4 to the upper case 1b is achieved by a fastening screw 6 which passes through the cover 1c.

Figure 2:
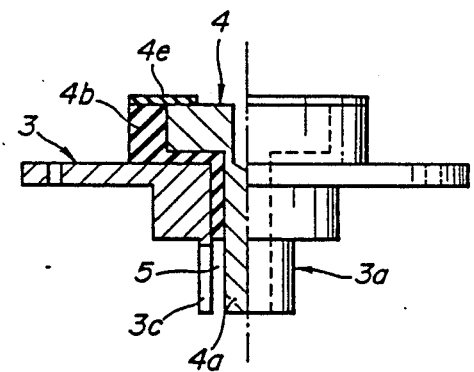
FIG. 2 is a partially sectioned front view of an electrode assembly mounted in the sensor of the first embodiment.
Figure 3:
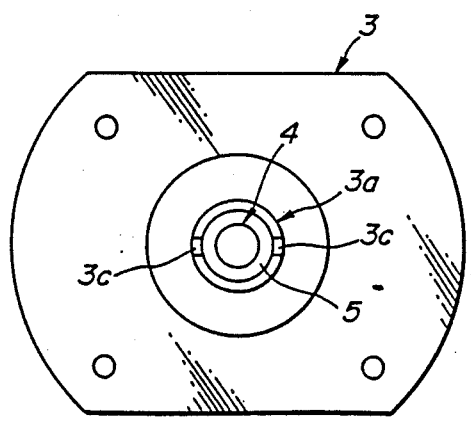
FIG. 3 is a bottom view of the electrode assembly.

As is seen from FIGS. 2 and 3, the cylindrical hollow probe portion 3a of the side electrode 3 is respective slits 3c which are aligned with respect to the axis of the fuel passage 1f.

Referring back to FIG. 1, an integrated circuit board whose base is denoted by numeral 8 is arranged in the cover 1c, which is connected to the lower and upper cases 1a and 1b by means of the afore-mentioned fastening screws 1d and 6. Electrically insulating spacers 8a and 8b are disposed between the base 8 and the upper case 1b, as shown. The base 8 has an integrated control circuit 7 disposed thereon.

Figure 4:
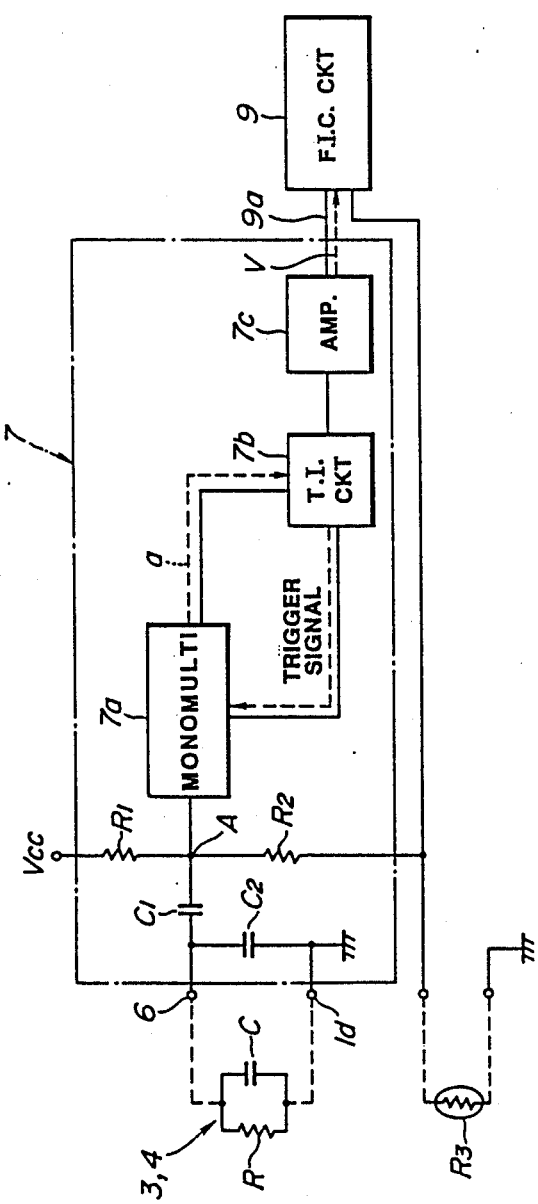
FIG. 4 is a control circuit employed in the invention.

The control circuit 7 functions to detect the capacitance established between the electrodes 3 and 4 and output an amplified voltage signal which varies in accordance with the methanol concentration in the mixed fuel. As is shown in FIG. 4, the control circuit 7 comprises condensers $C_1$ and $C_2$, resistors $R_1$ and $R_2$, a mono-multi (viz., monostable multivibrator) circuit 7a, a trigger and integrating circuit 7b and an amplifier 7c, which are connected in the illustrated manner. As shown, the junction between the condensers $C_1$ and $C_2$ is directly connected to the fastening screw 6, while the junction between the condenser $C_2$ and the ground is directly connected to the fastening screw 1d. It is to be noted that the fastening screws 6 and 1d are constructed of a good conductive material, such as copper or the like. A thermistor $R_3$ is connected to the resistor $R_2$, whose resistance varies in accordance with its surrounding temperature. The thermistor $R_3$ is located in the cylindrical space 5 of the afore-mentioned electrodes 3 and 4.

The control circuit 7 is connected through lead wires 9a to a known fuel injection control device 9. The control device 9 functions to control the fuel injection amount, air-fuel ratio of mixture fed to the engine and ignition timing in accordance with the voltage signal issued from the control circuit 7.

In the following, operation of the control circuit 7 will be described with reference to FIG. 4.

As shown in the drawing, the electrodes 3 and 4 are illustrated as a theoretical circuit which has both a capacitor C and a resistor R which are connected in parallel with the condenser $C_2$. The resistance of the resistor R is provided by the specified conductivity of methanol, which varies greatly depending on the amount of impurity, such as, ionized metal, water and the like, in the fuel. In order to minimize the effect of the resistance of the resistor R, the period for charging and discharging an after-mentioned charging and discharging circuit is determined less than 1 μsecond.

That is, the capacitor C, the resistor R, the thermistor $R_3$ and the mono-multi circuit 7a constitute the charging and discharging circuit. The trigger and integrating circuit 7b functions to issue a trigger signal to the mono-multi circuit 7a at a period of about 1 MHz and integrate a pulse signal "a" issued from the mono-multi circuit 7a.

When, thus, the mono-multi circuit 7a receives the trigger signal, the junction denoted by reference "A" shows zero potential causing the capacitor C to discharge its energy. Thereafter, the capacitor C is gradually charged through the resistor $R_1$.

Upon receiving the trigger signal, the output signal from the mono-multi circuit 7a becomes high level.

When, due to charging of the capacitor C, the potential of the junction "A" reaches a threshold voltage, the mono-multi circuit 7a is returned to its stable condition thereby causing the output signal to become low level.

After a given time, another trigger signal is issued from the trigger and integrating circuit 7b to carry out a similar operation in the circuit. Such operation is repeated as long as the trigger signal is issued by the circuit 7b.

That is, in response to the output of the trigger signal, the mono-multi circuit 7a issues the output pulse signal "a" whose pulse duration is proportional to the time for which the capacitor C has been charged.

The output pulse signal "a" from the circuit 7a is integrated by the trigger-integrating circuit 7b, and thus, the circuit 7b can issue an analog output in accordance with the charging time of the capacitor C. The analog output is amplified by the amplifier 7c to provide the fuel injection control device 9 with an amplified voltage signal "V". Based on the voltage signal "V" representative of the capacitance between the electrodes 3 and 4, the methanol concentration of the fuel is derived in the fuel injection control device 9.

In the following, operation of the fuel sensor of the first embodiment will be described.

According to the fuel sensor of the invention, the dielectric constant of the mixed fuel is detected by measuring the capacitance established between the electrodes, and the methanol concentration in the fuel is derived from the dielectric constant.

That is, the capacitance Cf established between the electrodes 3 and 4 is expressed by the following equation.

$$Cf = 2\pi \times \epsilon \times l / \log(b/a) \tag{1}$$

wherein:
ε: dielectric constant of a fuel,
a: radius of cylindrical solid probe portion 4a of center electrode 4,
b: radius of cylindrical hollow probe portion 3a of side electrode 3, and
l: length of each probe portion 3a or 4a.

The dielectric constant "ε" is represented by the following equation.

$$\epsilon = K \times \epsilon r \tag{2}$$

wherein:
εr: relative dielectric constant, and
K: constant.

Furthermore, the dielectric constant "εn" of a mixed fuel is expressed by the following equation.

$$\epsilon_n = (1-\alpha)\epsilon_A + \alpha\epsilon_B \tag{3}$$

wherein:
$\epsilon_A$: dielectric constant of fuel A,
$\epsilon_B$: dielectric constant of fuel B, and
α: mixing ratio of fuel B.

Thus, the capacitance established in the mixed fuel is derived by combining the equations (1) and (3). That is, by detecting the capacitance established between two electrodes 3 and 4, the mixing ratio "α", that is, the methanol concentration in the mixed fuel can be measured.

Experiments carried out by the inventors revealed that the constant "K" in the equation (2) is about $9 \times 10^{-12}$ F. In these experiments, parallel electrode plates of given sizes were submerged in methanol whose relative dielectric constant is known (viz., about 32.6) and the capacitance between the electrode plates was measured.

In the disclosed embodiment, the diameter of the fuel passage 1f is about 6 mm to 10 mm. This means that there is a limit in enlarging the size of the electrodes 3 and 4. Thus, if the probe portion of the electrode assembly has such a size that the diameter "a" of the center electrode is 0.0025 m, the internal diameter "b" of the side electrode is 0.005 m and the length "l" of the probe portion is 0.01 m, the first equation (1) and the above-mentioned revealed constant "K" allow the capacitance "Cf" between the two electrodes to be about $1.9 \times 10^{-12}$ F. which is very small.

It is now to be noted that, in the present invention, the transmission of such small-energy electric signal to the control circuit 7 is achieved by the electrically conductive fastening screws 6 and 1d each having a relatively short length. Thus, the harmful effects of noises and floating capacitance on the measuring performance can be suppressed or at least minimized in accordance with the present invention. Although the transmission of the output from the amplifier 7c to the fuel injection control device 9 is made through the lead wires 9a, such output is hardly affected by the noises and floating capacitance because the electric energy thereof is very higher than that of the noises and floating capacitance.

As is described hereinabove, in the fuel injection control device 9, the methanol concentration of the fuel is calculated based on the output from the amplifier 7c, and at the same time, corrections to the fuel injection control and ignition timing control are carried out.

Figure 5:
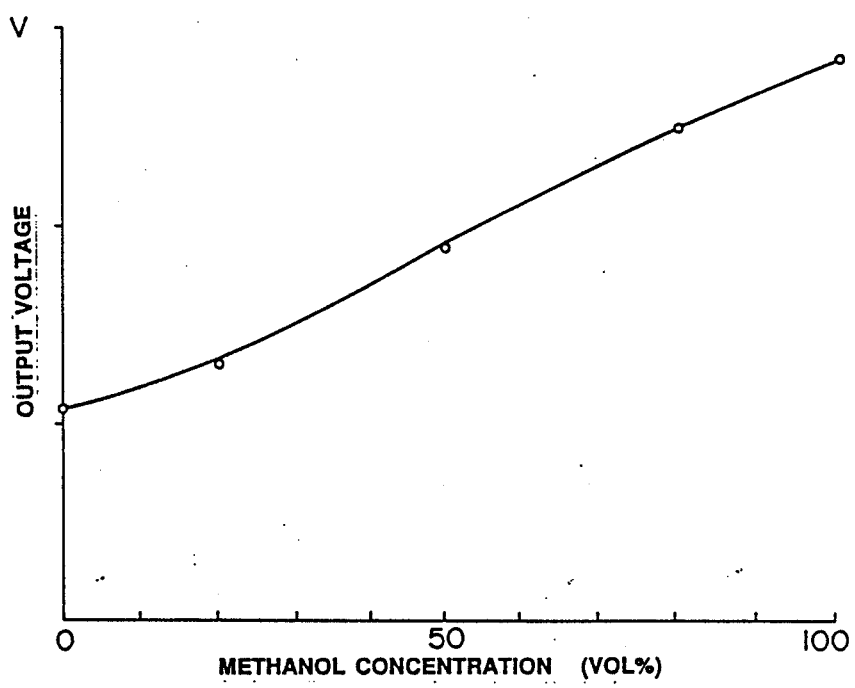
FIG. 5 is a graph showing the relationship between a methanol concentration in mixed fuel and amplified voltage output from the sensor.

FIG. 5 is a graph showing a relationship between the amplified voltage signal "V" issued from the amplifier 7c and the methanol concentration calculated in the fuel injection control device 9.

It is to be noted that, due to provision of the thermistor $R_3$ which is submerged in the fuel and connected to the junction "A" through the resistor $R_2$, the potential at the junction "A" is regulated in accordance with the temperature of the fuel. Thus, the measuring of methanol concentration in the fuel is achieved without being interrupted by the temperature change of the fuel.

Figure 6:
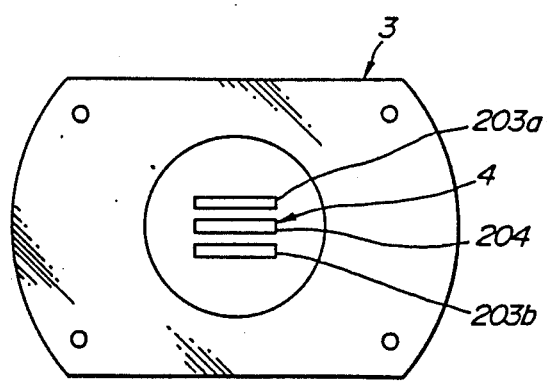
FIG. 6 is a view similar to FIG. 3, but showing a second embodiment of the present invention.

Referring to FIG. 6, there is shown, but in a bottom view, an electrode assembly employed in a second embodiment of the present invention.

In this second embodiment, the side electrode 3 has two flat probe portions 203a and 203b and the center electrode 4 has one flat probe portion 204, as shown. These probe portions are paralleled and arranged in parallel with the axis of the fuel passage 1f of the lower case 1a (see FIG. 1) having the center flat probe portion 204 spacedly put between the two side flat probe portions 203a and 203b. The remaining construction of the methanol sensor of this second embodiment is substantially the same as that of the afore-mentioned first embodiment.

In this second embodiment, the capacitance "C" established between the side and center electrodes 3 and 4 is represented by the following equation.

$$C = \epsilon \times S/d \qquad (4)$$

In the following, advantages of the present invention will be itemed.

First, since the electrode assembly and the integrated control circuit 7 are installed in a common housing 1, the length of electric conductors (viz., the fastening screws 6 and 1d) needed for electrically connecting these two electric parts can be shortened. This means that the harmful effects of noises and floating capacitance on the measuring performance of the sensor can be suppressed or at least minimized.

Second, since the fastening screws 6 and 1d for fastening the integrated circuit board 8 to the cases 1a and 1b serve as the conductors for the electric connection between the electrode assembly and the control circuit 7, the sensor can be constructed compact in size with reduced number of parts.

Third, since the output "V" from the sensor is amplified by the amplifier 7c to provide a voltage output before reaching the fuel injection control device 9, the effects of noises and floating capacitance on the information signal of the output are negligibly reduced.

Fourth, because of usage of the thermistor $R_3$, the measuring of methanol concentration in the fuel is achieved without being interrupted by temperature change of the fuel.

What is claimed is:

1. A fuel sensor for sensing a mixing ratio of a mixed fuel, said fuel sensor comprising:
   a housing;
   a structure disposed in said housing, said structure having a fuel passage formed therethrough;
   an electrode assembly disposed in said housing and held by said structure, said electrode assembly including paired electrodes which have respective probe portions exposed to said fuel passage;
   an integrated circuit board on which an output control circuit is disposed, said output control circuit issuing an amplified voltage output which varies in accordance with a small information signal applied to an input portion of said output control circuit; and
   at least two fastening screws connecting said integrated circuit board to said structure to form a tight mechanical connection therebetween said fastening screws constructed of electrically conductive material;
   wherein said fastening screws have respective upper portions directly in contact with mutually insulated sections of said input portion of said output control circuit, and respective lower portions directly in contact with said paired electrodes respectively.

2. A fuel sensor as claimed in claim 1, in which said electrode assembly further comprises:
   two side flat probe portions which are connected; and
   a center flat probe portion which is spacedly interposed between said two side flat probe portions.

3. A fuel sensor as claimed in claim 1, wherein one of said probe portions is formed as a cylindrical solid member and another of said probe portions is formed as a cylindrical hollow member, said solid member being coaxially disposed in said cylindrical hollow member, said cylindrical hollow member being provided, at diametrically opposed portions, the slits which are aligned along the axis of said fuel passage.

4. A fuel sensor as claimed in claim 3, in which said integrated circuit board comprises a base and an integrated control circuit disposed on said base.

5. A fuel sensor as claimed in claim 4, in which said output control circuit comprises:
- a monostable multivibrator circuit having an input connected to said electrode assembly;
- a trigger and integrating circuit connected to said monostable multivibrator circuit through two signal paths; and
- an amplifier having an input connected to said trigger and integrating circuit.

6. A fuel sensor as claimed in claim 5, in which said output control circuit further comprises a thermistor which is disposed in said fuel passage for making a correction to the output of said electrode assembly in accordance with the temperature of fuel which flows through said fuel passage.

7. A fuel sensor as claimed in claim 3, in which electrically insulating members are installed in said housing to assure insulation between said paired probe portions.

8. A fuel sensor as claimed in claim 7, in which seal rings are compressed between said electrode assembly and said structure to hermetically seal the interior of said housing from said fuel passage.

* * * * *